United States Patent
Ishino et al.

(10) Patent No.: US 7,663,069 B2
(45) Date of Patent: Feb. 16, 2010

(54) SWITCH STRUCTURE OF AUTOMATIC EXTERNAL DEFIBRILLATOR

(75) Inventors: Koji Ishino, Tokyo (JP); Kazunori Yoshifuku, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 12/354,726

(22) Filed: Jan. 15, 2009

(65) Prior Publication Data

US 2009/0178908 A1    Jul. 16, 2009

(30) Foreign Application Priority Data

Jan. 16, 2008    (JP) ............... 2008-006617

(51) Int. Cl.
*H01H 9/00* (2006.01)

(52) U.S. Cl. ............... 200/61.62; 200/333; 361/679.26; 361/679.27; 361/679.3

(58) Field of Classification Search ............. 200/61.62, 200/61.7, 61.71, 61.72, 61.74, 61.76, 43.16, 200/43.19, 43.21, 43.22, 318, 318.1, 321, 200/322, 333; 335/205–207; 361/679.26, 361/679.27, 679.3

See application file for complete search history.

(56) References Cited

U.S. PATENT DOCUMENTS

| | | | | |
|---|---|---|---|---|
| 3,622,720 A | * | 11/1971 | Allen | 200/50.1 |
| 5,191,970 A | * | 3/1993 | Brockway et al. | 200/335 |
| 5,268,674 A | * | 12/1993 | Howard et al. | 345/163 |
| 5,343,009 A | * | 8/1994 | Araoka et al. | 200/322 |
| 5,373,133 A | * | 12/1994 | Brockway et al. | 200/335 |
| 5,555,157 A | * | 9/1996 | Moller et al. | 361/679.3 |
| 6,301,501 B1 | * | 10/2001 | Cronin et al. | 607/5 |
| 6,704,194 B2 | * | 3/2004 | Koo | 361/679.27 |
| 6,891,722 B2 | * | 5/2005 | Chen et al. | 361/679.55 |
| 6,930,263 B2 | * | 8/2005 | Hung | 200/61.62 |
| 7,021,948 B2 | * | 4/2006 | Lin | 439/159 |
| 7,181,238 B2 | * | 2/2007 | Chiang | 455/556.1 |
| 2003/0208237 A1 | | 11/2003 | Locke et al. | |

* cited by examiner

*Primary Examiner*—Michael A Friedhofer
(74) *Attorney, Agent, or Firm*—Kimble Intellectual Property Law, PLLC

(57) ABSTRACT

A switch structure of an automatic external defibrillator including a housing member and a flap member for covering the housing member, open and closed states of the flap member and ON and OFF of a switch of the automatic external defibrillator which are associated with each other, the switch structure includes a movable unit for turning ON the switch when the flap member is in the open state and turning OFF the switch when the flap member is in the closed state and an operator performs further operation.

6 Claims, 2 Drawing Sheets

SWITCH STRUCTURE OF AUTOMATIC EXTERNAL DEFIBRILLATOR

BACKGROUND OF THE INVENTION

The present invention relates to a switch structure of an automatic external defibrillator.

Electric defibrillation of giving a strong electric shock to a heart for removing a twitch of the cardiac muscle is the most effective treatment for an asystole state caused by ventricular fibrillation. However, even if the electric defibrillation is conducted, the lifesaving possibility lowers about 7% to 10% every minute since occurrence of ventricular fibrillation and therefore a lifesaving treatment needs to be taken urgently as much as possible.

An automatic external defibrillator (AED) is used for the lifesaving treatment with the electric defibrillation.

The AED incorporates a computer and when electrode pads are attached on the chest of a patient, the AED automatically analyzes an electrocardiogram and determines whether or not electric defibrillation can be executed.

If the AED determines that electric defibrillation can be executed and the user operates an energizing switch in accordance with a command of the AED, the AED applies a voltage between the electrode pads and gives an electric shock to the heart of the patient.

To conduct the lifesaving treatment sequencer the AED guides the user along the lifesaving treatment procedure by voice, blinking of an operation button, etc., thereby enabling even any person other than medical service workers to conduct a lifesaving treatment comparatively easily.

As a domestic low is reformed so that even an ordinary citizen other than medical service workers can use the AED, every person will operate the AED in every scene. Since operation of the AED needs to be easy rather than complicated and the AED needs inform the operator of the operation situation, it is desirable that the main power supply of the AED should be easily turned ON.

To meet such a demand, there is the following AED. An operator presses a button, whereby a mechanical switch is turned ON and the main power supply is turned ON and a latch of a flap member covering a main unit is disengaged, opening the flap member (Refer to US2003/0208237A).

The AED described in US2003/0208237A has a structure for allowing an operator to press a button, whereby a mechanical switch is turned ON and the main power supply is turned ON and a latch of a flap member covering a main unit is disengaged, opening the flap member, so that the operator can easily turn ON the main power supply of the AED.

However, there is a problem in that the main power supply is turned OFF if the flap member is closed for some reason.

In the structure, the mechanical switch can be turned OFF even when the flap member is open. Thus, there is a problem in that the main power supply is turned OFF if the mechanical switch is turned OFF because of erroneous operation of the operator, etc., while the AED is being used.

If the main power supply is turned OFF while the AED is being used, the treatment of the AED before the main power supply is turned OFF is all canceled and the AED is again started from the beginning. Thus, it becomes difficult to deal with a situation in which a prompt treatment is needed. Therefore, it is desirable that the main power supply should be prevented from easily being turned OFF.

SUMMARY

It is therefore an object of the invention to provide a switch structure of an automatic external defibrillator in which a main power supply of an AED can be easily turned ON by an operator, if a flap member is closed for some reason, the main power supply is not turned OFF, and if an attempt is made to turn OFF a mechanical switch for a reason of erroneous operation of the operator, etc., when the AED is being used, the main power supply is not turned OFF.

In order to achieve the object, according to the invention, there is provided a switch structure of an automatic external defibrillator including a housing member and a flap member for covering the housing member, open and closed states of the flap member and ON and OFF of a switch of the automatic external defibrillator which are associated with each other, the switch structure comprising:

a movable unit for turning ON the switch when the flap member is in the open state and turning OFF the switch when the flap member is in the closed state and an operator performs further operation.

An opening may be formed with the housing member. A first member, which can be inserted in the opening, may project from the flap member. A second member may be urged towards the first member inserted in the opening. The movable unit may includes: a third member for opening the flap member and turning ON the switch; and a fourth member for allowing the third member to turn OFF the switch when the flap member is in a completely closed state in which the first member presses the second member against the spring.

The third member may be a knob which can slide between a closed position where the knob covers a part of the flap member in the completely closed state and an open position. When the third member is in the open position, the flap member may be opened and the switch is turned ON.

The third member and the housing member may be provided with a hall element for driving the switch and a magnet so that magnetic force of the magnet reaching the hall element monotonically changes in association with a sliding operation of the third member.

The switch may be turned OFF when the magnetic force of the magnet reaching the hall element becomes large.

The fourth member may be a blocking member abutting against the second member to prevent the third member from turning OFF the switch when the flap member is not in the completely closed state.

DETAILED DESCRIPTION OF PREFERRED EMBODIMENTS

The configuration of an AED of the invention will be discussed with FIGS. 1 and 2.

Figure 1:
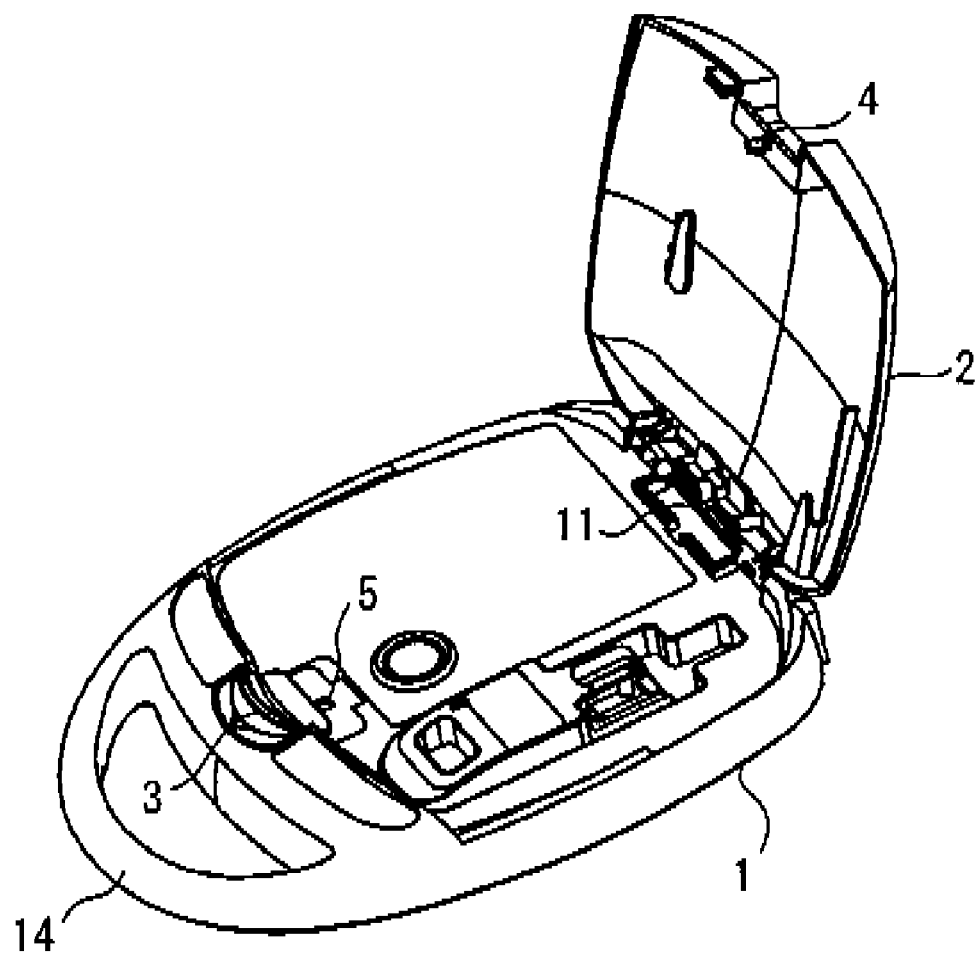
FIG. 1 is a perspective view to show the overall configuration of an AED of the invention.

In FIG. 1, numeral 1 denotes a main unit of the AED. The functional elements of the AED are built in the main unit, but do not directly relate to the invention and therefore will not be discussed again here.

Numeral 2 denotes a flap member covering the main unit. At the storage time of the AED, the flap member is closed for preventing entry of dust, etc.

Electrode pads are housed in the main unit, but not shown in the figure.

Numeral 3 denotes a slidable knob. An operator slides the knob when using the AED, whereby a spring 11 causes the flap member 2 to be opened as shown in the figure.

In the invention, the main power supply (not shown) of the AED is turned ON at the same time as the flap member 2 is opened as the operator slides the knob 3.

Numeral 4 denotes a projecting member formed on the flap member 2. The projecting member 4 corresponds to an opening hole 5 formed in the main unit 1.

Numeral 14 denotes a handle used for a portable purpose, etc.

Next, the configuration wherein the flap member 2 is opened and the main power supply of the AED is turned ON as an operator slides the knob 3 will be discussed with FIG. 2.

Figure 2:
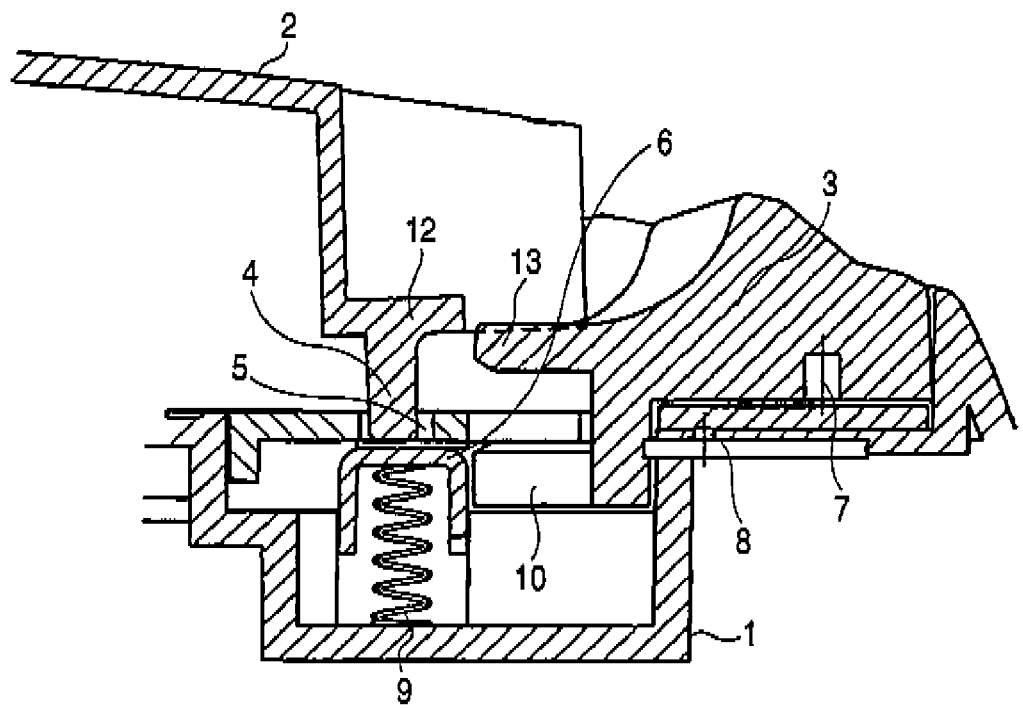
FIG. 2 is a sectional view of a switch structure to describe operation of turning ON a master electrical switch.

In FIG. 2, numeral 6 denotes a knob protector, numeral 7 denotes a magnet, numeral 8 denotes a hall element, numeral 9 denotes a spring, numeral 10 denotes a blocking member formed on the knob 3, numeral 12 denotes an engagement part provided in a part of the flap member 2, and numeral 13 denotes a latch part provided in the knob 3.

In the state in FIG. 2, the knob 3 is slid to an open position, engagement between the engagement part 12 of the flap member 2 and the latch part 13 of the knob 3 is released, and the flap member 2 is placed in an openable state. After this, the flap member 2 is completely opened by the spring 11 as shown in FIG. 1.

In the open state of the flap member 2 in FIG. 2, pressing the knob protector 6 by the projecting member 4 formed on the flap member 2 is released.

Therefore, the blocking member 10 exists on a side of the knob protector 6 and thus sliding the knob 3 (to the left in FIG. 2) is blocked and the main power supply cannot be turned OFF.

The positional relationship between the magnet 7 provided in the knob 3 and the hall element 8 for driving the master electrical switch provided in the main unit 1 shifts, whereby the main power supply is turned ON.

Next, the configuration in which the flap member 2 is closed and the main power supply of the AED is turned OFF by sliding the knob 3 will be discussed with FIG. 3.

Figure 3:
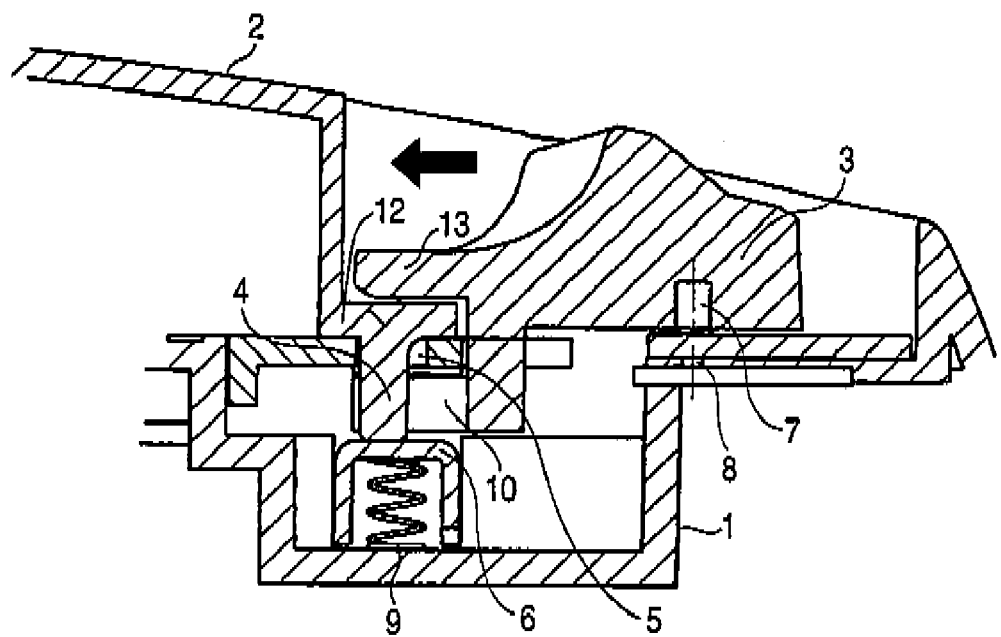
FIG. 3 is a sectional view of the switch structure to describe operation of turning OFF the master electrical switch.

In the state in FIG. 3, the knob 3 is slid in the arrow direction shown in FIG. 3 to a closed position, the flap member 2 is closed, the engagement part 12 of the flap member 2 and the latch part 13 of the knob 3 engage each other, and the flap member 2 is locked.

When an operator presses the flap member 2 downward from the state shown in FIG. 2, the projecting member 4 formed on the flap member 2 presses the knob protector 6, as shown in FIG. 3.

In the state shown in FIG. 3, the knob protector 6 is pressed and thus the blocking member 10 is not blocked and the knob 3 can be slid (to the left in FIG. 2) and the main power supply can be turned OFF.

The knob 3 is slid, whereby the magnet 7 provided in the knob 3 and the hall element 8 for driving the master electrical switch provided in the main unit 1 are opposed to each other and the main power supply is turned OFF.

A mechanical switch cannot be adopted as the master electrical switch because a water drop of a rain, etc., erodes the contact of the switch and the main power supply may he unable to be reliably turned ON at the necessary time.

Although it is also considered that a non-contact switch is adopted, an electrostatic proximity switch cannot be adopted because erroneous operation caused by charging can occur in summer, winter, etc., since a resin is used as a chassis of the AED is used.

Then, in an embodiment of the invention, a hall element is adopted for driving the master electrical switch of the AED.

The reason why the hall element is adopted for driving the master electrical switch of the AED is that the hall element has a characteristic that it is not affected by a water drop, etc., in the operation with a magnet as protection against a water drop of a rain, etc., is required because the AED may be used outdoors.

The reason why the main power supply is turned ON as the magnet is moved (slid) in the switch mechanism of the AED in FIGS. 2 and 3 is as follows:

When the hall element 8 and the magnet 7 are opposed to each other, the magnetic force of the magnet 7 reaching the hall element 8 is large and thus the electromotive force of the hall element 8 increases, keeping the main power supply OFF; when the magnet 7 shifts from the position of the hall element B, the magnetic force lessens and the electromotive force of the hall element 8 lessens, turning ON the main power supply.

The magnet 7 and the hall element 8 are opposed to each other to keep the main power supply OFF, but need not necessarily be opposed to each other. What is essential is that the magnet 7 and the hall element 8 may be provided so that the magnetic force of the magnet 7 reaching the hall element 8 monotonically changes in response to the slide between the closed and open positions of the knob 3. However, the most of the magnetic force of the magnet 7 can be made by opposing the magnet 7 and the hall element 8 to each other as in the embodiment.

In the switch mechanism of the AED in FIGS. 2 and 3, when the hall element 8 and the magnet 7 are opposed to each other, the main power supply is kept OFF and when the magnet 7 shifts from the position of the hall element 8, the main power supply is turned ON. However, the operation can also be inverted in such a manner that when the hall element 8 and the magnet 7 are opposed to each other, the main power supply is kept ON and that when the magnet 7 shifts from the position of the hall element 9, the main power supply is turned OFF.

However, considering the importance of the main power supply in the AED, it is desirable that the configuration as shown in FIGS. 2 and 3 as fail sate for turning ON the main power supply for making the AED usable if the hall element fails (magnetism cannot be detected, etc.,) should be adopted.

Although it is also possible to drive the master electrical switch by a photosensor using light having a similar function to that of the hall element, the photosensor requires a light source and the light source is operated and thus the battery shelf life is affected.

Since the battery shelf life is important for the AED placing importance on small size and lightweight, driving the master electrical switch using the magnet and the hall element is excellent in this point.

Next, the operation of the master electrical switch of the AED of the invention operated by the operator when using the AED is as follows:

To use the AED, the operator slides the knob 3 to a side of the handle 14 (Step S1).

As the knob is slid at step S1, the engagement part 12 of the flap member 2 locked by the latch part 13 of the knob 3 is released and the flap member 2 is opened and the magnet 7 provided in the knob 3 shifts from the position opposed to the hall element 8 and the main power supply of the AED is turned ON (Step S2).

In this state, the projecting member 4 formed on the flap member 2 appears outside the opening hole 5 of the main unit 1 and thus pressing the knob protector 6 by the projecting member 4 is released and the knob protector 6 moves upward because of the restitution force of the spring 9 (the state in FIG. 2) (Step S3).

In this state, if the flap member 2 is simply closed for some reason (erroneous operation of the operator, etc.,), the magnet 7 and the hole element S are not placed at the opposed position and thus the main power supply is not turned OFF.

In this state, if an attempt is made to slide the knob 3 for some reason (erroneous operation of the operator, etc.,), the blocking member 10 formed on the knob 3 strikes the knob protector 6 and the knob 3 cannot be slid and thus the magnet 7 and the hole element 8 are not placed at the opposed position and thus the main power supply is not turned OFF.

Next, to turn OFF the master electrical switch of the AED at the termination of using the AED, the operator closes the flap member 2 (Step S4).

If the operator presses the flap member 2 when the flap member 2 is closed at step S4, the projecting member 4 formed on the flap member 2 presses the knob protector 6 of the main unit 1 against the restitution force of the spring 9 (Step S5).

In the state at step S5, the knob protector 6 is pressed and the blocking member 10 formed on the knob 3 can be slid in the arrow direction and thus the knob 3 is slid in the arrow direction (the state in FIG. 3) (Step S6).

As the knob 3 is slid at step S6, the latch part 13 of the knob 3 and the engagement part 12 of the flap member 2 engage each other and the flap member 2 is completely closed and the magnet 7 and the hall element 8 are opposed to each other and the main power supply of the AED is turned OFF.

As described above, the operator can easily turn ON the main power supply of the AED of the invention simply by operating the flap member using the knob.

However, if the flap member is simply closed for some reason (erroneous operation of the operator, etc.,) or if an attempt is made simply to slide the knob in the OFF direction for some reason (erroneous operation of the operator, etc.,) when the AED is being used, the main power supply is not turned OFF.

To turn OFF the main power supply of the AED, it is necessary to slide the knob in the OFF direction in a state in which the operator presses the flap member in the closed state.

According to the invention, the operator can easily turn ON the main power supply of the AED and if the flap member is closed for some reason, the main power supply is not turned OFF.

The invention produces the particular advantage that if an attempt is made to turn OFF the mechanical switch for a reason of erroneous operation of the operator, etc., when the AED is being used, the main power supply is not turned OFF and only if the operator performs further operation with the flap member closed, the master electrical switch is turned OFF.

What is claimed is:

1. A switch structure of an automatic external defibrillator including a housing member and a flap member for covering the housing member, open and closed states of the flap member and ON and OFF of a switch of the automatic external defibrillator which are associated with each other, the switch structure comprising:
   a movable unit for turning ON the switch when the flap member is in the open state and turning OFF the switch when the flap member is in the closed state and an operator performs further operation.

2. The switch structure as claimed in claim 1, wherein an opening is formed with the housing member,
   a first member, which can be inserted in the opening, projects from the flap member,
   a second member is urged towards the first member inserted in the opening, and
   the movable unit includes:
      a third member for opening the flap member and turning ON the switch; and
      a fourth member for allowing the third member to turn OFF the switch when the flap member is in a completely closed state in which the first member presses the second member against the spring.

3. The switch structure as claimed in claim 2, wherein the third member is a knob which can slide between a closed position where the knob covers a part of the flap member in the completely closed state and an open position, and
   when the third member is in the open position, the flap member is opened and the switch is turned ON.

4. The switch structure as claimed in claim 3, wherein the third member and the housing member are provided with a hall element for driving the switch and a magnet so that magnetic force of the magnet reaching the hall element monotonically changes in association with a sliding operation of the third member.

5. The switch structure as claimed in claim 4, wherein the switch is turned OFF when the magnetic force of the magnet reaching the hall element becomes large.

6. The switch structure as claimed in claim 2, wherein the fourth member is a blocking member abutting against the second member to prevent the third member from turning OFF the switch when the flap member is not in the completely closed state.

* * * * *